(12) United States Patent
Bjellqvist et al.

(10) Patent No.: US 7,943,029 B2
(45) Date of Patent: May 17, 2011

(54) METHOD, COMPOSITION AND KIT FOR ISOELECTRIC FOCUSING

(75) Inventors: Bengt Bjellqvist, Stockholm (SE); Henrik Neu, Uppsala (SE); Kristina Uhlen, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 352 days.

(21) Appl. No.: 12/161,012

(22) PCT Filed: Jan. 30, 2007

(86) PCT No.: PCT/SE2007/000078
§ 371 (c)(1), (2), (4) Date: Jul. 16, 2008

(87) PCT Pub. No.: WO2007/089188
PCT Pub. Date: Aug. 9, 2007

(65) Prior Publication Data
US 2009/0026081 A1    Jan. 29, 2009

(30) Foreign Application Priority Data
Jan. 31, 2006 (SE) ...................................... 0600236

(51) Int. Cl.
*C07K 1/28* (2006.01)
(52) U.S. Cl. ........................................ 204/548; 204/644
(58) Field of Classification Search .................. 204/548, 204/644
See application file for complete search history.

(56) References Cited

FOREIGN PATENT DOCUMENTS
WO    WO2005/103070    11/2005

OTHER PUBLICATIONS

Johnsson, B., et al. "Comparison of methods for immobilization to carboxymethyl dextran sensor surfaces by analysis of the specific activity of monoclonal antibodies" Journal of Molecular Recognition, vol. 8, 1995, p. 125-131.*
Gianazza, E., et al. "Formulations for immobilized pH gradients including pH extremes" Electrophoresis, vol. 10, 1989, p. 806-808.*
Bier, M., et al., "Recycling isoelectric focusing: use of simple buffers" Journal of Chromatography, 604 (1992) 73-83.
Frey, M., et al., "High Resolution preparative isoelectric focusing in layers of granulated gels" Electrophoresis, 3 (1982) 216-266.
Yang, C., et al., "Repeatedly usable immobilized pH gradient in a monolithic capillary column" Electrophoresis, 25 (2004) 1729-1734.

* cited by examiner

*Primary Examiner* — Ula C Ruddock
*Assistant Examiner* — J. Christopher Ball
(74) *Attorney, Agent, or Firm* — Yonggang Ji

(57) ABSTRACT

The present invention relates to a method, composition and a kit for isoelectric focusing. More closely, the present invention involves the use of to modified carrier ampholytes which are easy to separate from the proteins/peptides following finished focusing. The modification is that the carrier ampholytes are derivatised with handles interacting with a solid phase/matrix which makes them easy to remove and separate from the peptides after finished focusing. In this way, there is very little or no background from carrier ampholytes in the following MS-spectra.

16 Claims, No Drawings

METHOD, COMPOSITION AND KIT FOR ISOELECTRIC FOCUSING

CROSS-REFERENCE TO RELATED APPLICATIONS

This application is a filing under 35 U.S.C. §371 and claims priority to international patent application number PCT/SE2007/000078 filed Jan. 30, 2007, published on Aug. 9, 2007, as WO 2007/089188, which claims priority to patent application number 0600236-4 filed in Sweden on Jan. 31, 2006.

FIELD OF THE INVENTION

The present invention relates to a method, a composition and a kit for isoelectric focusing. More closely, the present invention involves the use of modified carrier ampholytes which are easy to separate from the proteins/peptides following finished focusing.

BACKGROUND OF THE INVENTION

The isolation of biomolecules, such as proteins and peptides, has become of an increased interest during the past years. Some biomolecules need to be isolated as a last step of a biotechnological method for the production thereof, for example in the preparation of protein or peptide-based pharmaceutical compounds. Similarly there is also a need to separate biomolecules for analytical purposes in order to be able to quantify and identify the proteins and/or peptides present in a sample.

For identification and characterization of separated proteins mass spectrometry (MS) methods are normally used. A sample applied to a MALDI (Matrix Assisted Laser Desorption Ionization) MS target is only allowed to contain a limited number of peptides and similarly ESI (electrospray ionization) -MS can only accept a limited number of peptides per time unit. The sample is normally a very complex mixture containing many thousand of proteins which after digestion could easily correspond to one hundred thousand to more than one million peptides. There is therefore a need for rigorous separation of the peptides prior to MS characterization and quantification. A variety of different separation methods including electrophoretic and chromatographic methods can be used; normally multiple separation steps are required.

Generally electrophoretic techniques like isoelectric focusing (IEF) and sodium dodecyl sulphate (SDS) electrophoresis give, when used at the protein level in gel, much better resolution and protein yields than chromatographic alternatives. 2-D electrophoresis based on the combination of these two techniques, IEF and SDS, is also a commonly used approach when separation of very complex samples is conducted at the protein level.

In isoelectric focusing (IEF), the separation takes place in a pH gradient that occupies the whole separation distance and is arranged so that the pH in the gradient increases from anode towards the cathode. While other alternatives also exist, the pH gradients required in isoelectric focusing are in practice generated in two different ways: with the aid of a solution of carrier ampholytes or with an immobilized pH gradient. Carrier ampholytes are a spectrum of low molecular weight ampholytes with closely spaced isoelectric points. The carrier ampholytes give a good and regular conductivity at the isoelectric point and can carry the current during focusing.

In the case of an immobilized pH gradient (IPG) the charged or chargeable groups generating the pH gradient are bound either to the wall of a capillary system or to the matrix when some kind of gel is used to get convection stabilization. The immobilized charged or chargeable groups used are normally a limited number of carboxylic groups or amino groups with different pK-values distributed within or close to the pH gradient, which is to be generated. The concentration of the charged or chargeable groups is varied along the separation distance in a manner causing the pH at which the wall or the gel matrix has a zero net charge to increase from the anode to the cathode. A commercially available example of a system for generation of immobilized pH gradients is the IMMOBILINE II SYSTEM™(Amersham Biosciences, Uppsala, Sweden), wherein a pH gradient covalently attached to a polyacrylamide gel is formed. Immobilized pH gradients are truly stationary and today they are normally used together with carrier ampholytes. In this combination the immobilized gradient determines the resulting pH gradient, while the carrier ampholytes contribute with conductivity.

Focusing of peptides in presence of carrier ampholytes (PHARMALYTE™, AMPHOLINE™ or IPG (immobilized pH gradient)-buffer) result in sharper better focused peptide bands than when focusing is done in the absence of carrier ampholytes. The carrier ampholytes and the peptides both represents mixtures of large numbers of amphoteric compounds and the properties are partly very similar, which make it difficult to completely separate the to types of amphoteric compounds after finished focusing. A presently used approach is to trap the peptides on a reversed phase column and wash away the carrier ampholyte. However, this procedure results in the loss of some peptides together with the carrier ampholytes, while other carrier ampholyte compounds are bound with the peptides to the column. When released together with the peptides these latter ampholytes will generate a background in the mass spectrum used for quantification and/or identification of peptides.

Of existing methods for peptide separation, isoelectric focusing in IPG strips is the method, which gives the highest resolution and the best reproducibility. But as appears above, there is a need for improvement within this field.

SUMMARY OF THE INVENTION

The present invention provides an alternative to using the common carrier ampholytes when focusing peptides in IPG gels or strips.

The present invention provides novel carrier ampholytes which are derivatised with compounds having specific properties; below these ampholytes are called derivatised ampholytes. According to the present invention the derivatised ampholytes are provided with compounds acting as handles or tags to allow a fast, easy and complete removal of the derivatised ampholytes from peptides after finished IEF by using the properties of the handles to interact with a matrix/solid support and thereby separate the derivatised ampholytes from the peptides, wherein the derivatised ampholytes become bound to the matrix/solid support and the peptides remain unbound and can be further analyzed without interference from the carrier ampholytes.

Thus, in a first aspect the invention relates to a method of running isoelectric focusing comprising focusing of peptides in the presence of derivatised carrier ampholytes, wherein the derivatised carrier ampholytes are provided with handles for easy removal thereof after focusing by interaction between the handles and a matrix/solid support.

The derivatised carrier ampholytes are removed from the peptides by adhering, adsorbing or binding to the matrix/solid phase. Thus, the handle may be an adherence unit, adsorption unit or binding unit.

The adherence, adsorption or binding of the handle to the solid phase may be directly to the solid phase, i.e. to the solid phase per se, or to structures provided on the solid phase surface.

Preferably, the removal is by chromatography wherein the matrix/solid phase is a chromatographic media such as an affinity media and the handle or ligand is of a type which interacts and reversibly adheres to such media.

In another embodiment, the method is performed wherein the derivatised carrier ampholytes are removed in solution by settling and removing the solid phase or by centrifuging and removing the solid phase.

In a second aspect, the invention relates to a composition for peptide focusing comprising a mixture of carrier ampholytes which are derivatised with compounds or handles having the properties of interacting with a solid phase/matrix.

The handle is immobilized or otherwise coupled to the carrier ampholyte. The handle may be any handle that does not interfere with the IEF process and interacts with a solid phase and may be, for example, chosen from a member of a red-ox pair, such as disulfide, or from an affinity pair, such as biotin-avidin, or from an antigen-antibody pair, wherein the antibody alternatively also could be a fragment of an antibody.

As the thiol groups in the peptides normally are blocked prior to the tryptic digestion, a preferred alternative is to introduce thiol groups as handles into the carrier ampholytes. Thereafter, activated thiol bound on a solid phase such as thiopropyl or thiol SEPHAROSE™, can be used to, by oxidative addition, eliminate the carrier ampholytes from focused peptide fractions.

Another alternative is to bind biotin to the carrier ampholytes and to use the biotin-avidin/streptavidin interaction for elimination of carrier ampholytes.

In a third aspect, the invention relates to a kit comprising the compositions according to the present invention and IPG strips for peptide focusing. The IPG strips could be Ready-To-Go or in a dry state to be re-hydrated upon use.

DETAILED DESCRIPTION OF THE INVENTION

Below the invention is described in an exemplifying way which is not to be regarded as limiting for the scope of the invention.

Preparation of Derivatised Carrier Ampholytes

The presently preferred modification of the carrier ampholytes is a thiol-ampholyte.

The thiol containing ampholyte is generated by dissolving ammoniumchloride (1.3 eq), beta-alanin (2.7 eq), glycin (1 eq), glycylglycin (2 eq), 6-aminocaproic acid (2.7 eq), 4-aminobutyric acid (2.7 eq), iminodiacetic acid (2.3 eq), DL-glutamic acid (2.3 eq), DL-aspartic acid (2.7 eq) and homo-cystine (1.3 eq) in distilled water. After stirring for 1.5 hours the temperature is raised to 48° C. and the pH was raised to 10 by addition of 8M NaOH. Epichlorohydrin (17 eq) was then added in 2 mL portions every 5 minutes over 1 hour for a controlled polymerization. pH was continuously adjusted to 10 by a total of 44 eq during the epichlorohydrin addition. The reaction was left at 48° C. for one hour and then slowly cooled to room temperature over night. The next day the reaction mixture is neutralized using HCl (6 M) and filtered over a 45 μm filter.

The filtrated ampholyte mixture was adjusted to pH 7.9 followed by addition of TCEP (0.9 eq) and the mixture was stirred for one hour. A thiopropyl SEPHAROSE™ gel was conditioned and added to the ampholyte solution and the resulting gel was stirred at room temperature over night. The gel was filtrated on a glass filter and washed with a TRIS buffer pH 7.9. The thiol containing ampholyte was then eluted using a TRIS buffer with dithiothreitol. The eluate was collected, freeze dried followed by salt removal. The ampholyte was then titrated to determine the buffer capacity.

Optionally the carrier ampholytes are purified using size exclusion and after reductive cleavage of the S—S bond of homo-cystine the free thiol will be trapped on a SEPHAROSE™ thiol column. After washing of the column, mild reductive elution of the carrier ampholytes bearing the thiol group is performed and enriched thiol carrier ampholyte is obtained.

IEF Procedure Using the Derivatised Ampholyte

A dried IEF gel is used which is rehydrated in rehydration solution before use. The thiol-ampholyte or other derivatised ampholyte according to the invention is provided (1-5 w/w %) in the rehydration solution and optionally also in the sample buffer. If the sample is not rehydrated into the dry gel, then it is applied to the rehydrated gel by cup or paper bridge loading.

Following focusing the focused fractions are separately extracted from the IEF strip into a solution phase. Thereafter, the fractions are transferred to a micro titre plate.

Removal of Carrier Ampholyte

Each fraction in the micro titre plate is purified on an activated thiopropyl or thiol Sepharose column to remove the derivatised carrier ampholytes from the peptides. The derivatised carrier ampholytes will stay on the column while the peptides will flow through.

Analysis of Peptides

The peptide fraction is thereafter transferred to a reverse phase (RPC) column and finally MS is run for identification of peptides.

By using the derivatised carrier ampholytes according to the invention, the background in the mass spectrum can be lowered compared to using conventional carrier ampholytes. Therefore the quantification and/or identification of peptides is improved compared to prior art.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

The invention claimed is:

1. A method of running isoelectric focusing, comprising focusing of peptides in the presence of derivatised carrier ampholytes, wherein the derivatised carrier ampholytes are provided with handles, the method further comprising removal of the derivatised carrier ampholytes from the peptides after focusing wherein the handles are a member chosen from a group comprising a red-ox pair, an affinity pair, and an antigen-antibody pair.

2. The method of claim 1, wherein the derivatised carrier ampholytes are removed by adhering, adsorbing or binding to a solid phase interacting with the handles.

3. The method of claim 2, wherein the derivatised carrier ampholytes are removed in solution by settling and removing the solid phase or by centrifuging and removing the solid phase.

4. The method of claim 2, wherein the derivatised carrier ampholytes are removed by chromatography.

5. The method of claim 4, wherein the derivatised carrier ampholytes are removed by affinity chromatography.

6. The method of claim 5, wherein the handle is a member of an affinity pair.

7. The method of claim 6, wherein the handle is a biotin-group.

8. The method of claim 1, wherein the handle is a member of a red-ox pair.

9. The method of claim 8, wherein the handle is a thiol-group.

10. A composition comprising a mixture of carrier ampholytes derivatised with handles interacting with a solid phase wherein the handles are a member chosen from a group comprising a red-ox pair, an affinity pair, and an antigen-antibody pair.

11. The composition of claim 10, wherein the handles are selected from a member of an affinity pair or from a member of a red-ox pair.

12. The composition of claim 11, wherein the handle is a thiol-group.

13. The composition of claim 11, wherein the handle is a biotin-group.

14. A kit comprising the composition of claim 10 and a IPG (immobilized pH gradient) gel or strip.

15. The kit of claim 14, wherein the gel or strip is pre-cast.

16. The kit of claim 14, wherein the gel or strip is dried.

* * * * *